US007968300B2

(12) United States Patent
Chin et al.

(10) Patent No.: US 7,968,300 B2
(45) Date of Patent: Jun. 28, 2011

(54) METHOD OF ISOLATING REGULATORY T CELLS FROM HUMAN SAMPLES

(76) Inventors: Li-Te Chin, Hsinchu (TW); Shu-Ching Hsu, Yanchao (TW)

(*) Notice: Subject to any disclaimer, the term of this patent is extended or adjusted under 35 U.S.C. 154(b) by 187 days.

(21) Appl. No.: 11/943,682

(22) Filed: Nov. 21, 2007

(65) Prior Publication Data

US 2009/0214553 A1 Aug. 27, 2009

(51) Int. Cl.
*G01N 33/53* (2006.01)
(52) U.S. Cl. ....................................................... 435/7.1
(58) Field of Classification Search .................... None
See application file for complete search history.

(56) References Cited

U.S. PATENT DOCUMENTS

| | | | |
|---|---|---|---|
| 5,811,097 A | 9/1998 | Allison et al. | |
| 5,855,887 A | 1/1999 | Allison et al. | |
| 6,051,227 A | 4/2000 | Allison et al. | |
| 6,207,156 B1 | 3/2001 | Kuchroo et al. | |
| 6,228,361 B1 | 5/2001 | Posner | |
| 7,229,628 B1 | 6/2007 | Allison et al. | |
| 2003/0049696 A1* | 3/2003 | Norment et al. ............. | 435/7.21 |

FOREIGN PATENT DOCUMENTS

| | | |
|---|---|---|
| WO | WO 2007/117602 | 2/2005 |
| WO | WO 2005/012495 | 10/2007 |

OTHER PUBLICATIONS

Alegre et al., Nat. Rev. Immunol., 2001, 1: 220-228.*
Birebent, B, et al, 2004, "Suppressive properties of human CD4+CD25+ regulatory T cells are dependent on CTLA-4 expression," Eur. J. Immunol., 34:3485-96.
Burstein, S and Knapp, R, 1977, "Chemotherapy of murine ovarian carcinoma by methotrexate-antibody conjugates," J. Med. Chem., 20:950-2.
Chikuma, S and Bluestone, JA, 2002, "CTLA-4: acting at the synapse," Mol. Interv., 2:205-8.
Chin, LT, et al, 2001, "Establishment and evaluation of mouse-human heteromyeloma cell lines obtained by electrofusion for immortalizing human immunoglobulins," J. Biom.
Chin, LT, et al, 2007, Site-directed in vitro immunization leads to a complete human monoclonal IgG4 lambda that binds specifically to the CDR2 region of CTLA-4 (CD152.
Dannull, J, et al, 2005, "Enhancement of vaccine-mediated antitumor immunity in cancer patients after depletion of regulatory T cells," J. Clin. Invest., 115:3623-33.
Davis, DM and Dustin, ML, 2004, "What is the importance of the immunological synapse?" Trends Immunol., 25:323-7.
Duenas M, et al, 1996, "In vitro immunization of naive human B cells yields high affinity immunoglobulin G antibodies as illustrated by phage display," Immunology, 89:1.
Dustin, ML, 2002, "The immunological synapse," Arthritis Res., 4 Suppl 3: S119-25.
Egen, JG and Allison, JP, 2002, "Cytotoxic T lymphocyte antigen-4 accumulation in the immunological synapse is regulated by TCR signal strength," Immunity, 16:23-35.

Egen, JG, et al, 2002, "CTLA-4: new insights into its biological function and use in tumor immunotherapy," Nat. Immunol., 3:611-8.
Gough, SC, et al, 2005, "CTLA4 gene polymorphism and autoimmunity," Immunol. Rev., 204:102-15.
Grakoui, A, et al, 1999, "The immunological synapse: a molecular machine controlling T cell activation," Science, 285:221-7.
Hori, S, et al, 2003, "Control of regulatory T cell development by the transcription factor Foxp3," Science, 299:1057-61.
Krummel, MF and Allison, JP, 1996,"CTLA-4 engagement inhibits IL-2 accumulation and cell cycle progression upon activation of resting T cells," J. Exp. Med., 183:2533-4.
Linsley, PS, et al, 1991, "CTLA-4 is a second receptor for the B cell activation antigen B7," J. Exp. Med., 174:561-9.
Linsley, PS, et al, 1992, "Coexpression and functional cooperation of CTLA-4 and CD28 on activated T lymphocytes," J. Exp. Med., 176:1595-604.
Lopes, JE, et al, 2006, "Analysis of FOXP3 reveals multiple domains required for its function as a transcriptional repressor," J. Immunol., 177, 3133-42.
Magistrelli, G, et al, 1999, "A soluble form of CTLA-4 generated by alternative splicing is expressed by nonstimulated human T cells," Eur. J. Immunol., 29:3596-602.
Nistico, L, et al, 1996, "The CTLA-4 gene region of chromosome 2q33 is linked to, and associated with, type 1 diabetes. Belgian Diabetes Registry," Hum. Mol. Genet., 5: pp. 1075-1080.
Oaks, MK and Hallett, KM, 2000, "A soluble form of CTLA-4 in patients with autoimmune thyroid disease," J. Immunol., 164:5015-8.
Oaks, MK, et al, 2000, "A native soluble form of CTLA-4," Cell. Immunol., 201:144-53.
Peach, RJ, et al, 1994, "Complementarity determining region 1 (CDR1)- and CDR3-analogous regions in CTLA-4 and CD28 determine the binding to B7-1," J. Exp. Med., 180:20.
Pioli, C, et al, 2000, "Inhibition of IgG1 and IgE production by stimulation of the B cell CTLA-4 receptor" J. Immunol., 165:5530-6.
Prud'homme, GJ, 2004, "Altering immune tolerance therapeutically: the power of negative thinking," J. Leukoc. Biol., 75:586-99.
Qi, SY, et al, 2001, "Synaptic pattern formation during cellular recognition," Proc. Natl. Acad. Sci. USA, 98:6548-53.
Rao, A, et al, 2007, "Successful bone marrow transplantation for IPEX syndrome after reduced-intensity conditioning," Blood, 109:383-5.
Read, S, et al, 2006, "Blockade of CTLA-4 on CD4+CD25+ regulatory T cells abrogates their function in vivo," J. Immunol., 177:4376-83.
Sakaguchi, S, 2005, "Naturally arising Foxp3-expressing CD25+CD4+ regulatory T cells in immunological tolerance to self and non-self," Nat. Immunol., 6:345-52.

(Continued)

*Primary Examiner* — Ilia Ouspenski

(74) *Attorney, Agent, or Firm* — Ming Chow; Sinorica, LLC

(57) ABSTRACT

The present invention provides a CTLA-4 non-blocking agent of a complete human antibody nature, thus is non-immunogenic in a human. The immunoassay method using such a non-blocking agent measures the CTLA-4 content in a sample of a human subject. The present invention further provides a novel method for isolating human regulatory T cells. The resultant enriched and depleted cellular populations are useful in treating or ameliorating of human diseases.

3 Claims, 6 Drawing Sheets

OTHER PUBLICATIONS

Sato, S, et al, 2004, "Serum soluble CTLA-4 levels are increased in diffuse cutaneous systemic sclerosis," Rheumatology, 43:1261-6.

Schwartz, JC, et al, 2001, "Structural basis for co-stimulation by the human CTLA-4/B7-2 complex," Nature, 410:604-8.

Sharpe, AH and Freeman, GJ, 2002, "The B7-CD28 superfamily" Nat. Rev. Immunol., 2:116-26.

Stamper, CC, et al, 2001, "Crystal structure of the B7-1/CTLA-4 complex that inhibits human immune responses," Nature, 410:608-11.

Steiner, K, et al, 1999, "Enhanced expression of CTLA-4 (CD152) on CD4+ T cells in HIV infection," Clin. Exp. Immunol., 115:451-7.

Takahashi, T, et al, 2000, Immunologic self-tolerance maintained by CD25(+)CD4(+) regulatory T cells constitutively expressing cytotoxic T lymphocyte-associated antige.

Tivol, EA, et al, 1995, Loss of CTLA-4 leads to massive lymphoproliferation and fatal multiorgan tissue destruction, revealing a critical negative regulatory role of C.

von Boehmer, H, 2005, "Mechanisms of suppression by suppressor T cells," Nat. Immunol., 6:338-44.

Wang, S and Chen, L, 2004, "T lymphocyte co-signaling pathways of the B7-CD28 family," Cell. Mol. Immunol., 1:37-42.

Ward, FJ and Barker, RN, 2007, "Soluble CTLA-4 responses—a novel mechanism for regulatory T cell suppression?" Immunology, 120, Suppl:9 (meeting abstract).

Wildin, RS and Freitas, A, 2005, "IPEX and FOXP3: clinical and research perspectives," J. Autoimmun., 25 Suppl:56-62.

Wong, CK, et al, 2005, "Aberrant production of soluble costimulatory molecules CTLA-4, CD28, CD80 and CD86 in patients with systemic lupus erythematosus," Rheumatology.

[0050] Wong, CK, et al, 2005, "Increased expression of plasma and cell surface co-stimulatory molecules CTLA-4, CD28 and CD86 in adult patients with allergic asthma," Clin. Ex.

Wu, Y, et al, 2006, "FOXP3 controls regulatory T cell function through cooperation with NFAT," Cell, 126:375-87.

Xystrakis, E, et al, 2004, "Identification of a novel natural regulatory CD8 T-cell subset and analysis of its mechanism of regulation," Blood, 104:3294-301.

* cited by examiner

```
                  -35                                                          1                                  25
Isoform A    MACLGFQRHK   AQLNLATRTW   PCTLLFFLLF   IPVFCKAMHV   AQPAVVLASS   RGIASFVCEY
Isoform B    **********   **********   **********   **********   **********   **********

CDR1                                  CDR2
                          ⎰‾‾‾‾‾‾‾‾‾⎱                            →
             26                                                                            85
Isoform A    ASPGKATEVR   VTVLRQADSQ   VTEVCAATYM   MGNELTFLDD   SICTGTSSGN   QVNLTIQGLR
Isoform B    **********   **********   **********   **********   **********   **********

CDR3
                                                   ⎰‾‾‾‾‾‾‾‾‾
             86                                                                            145
Isoform A    AMDTGLYICK   VELMYPPPYY   LGIGNGTQIY   VIDPEPCPDS   DFLLWILAAV   SSGLFFYSFL
Isoform B    ********   ******   ******   ******   AKEKKPSY   NRGLCENAPN   RARM 146                                                        188
Isoform A    LTAVSLSKML   KKRSPLTTGV   YVKMPPTEPE   CEKQFQPYFI   PIN
```

*FIG. 1*

SEQUENCE LISTING

```
<160> NUMBER OF SEQ ID NOS: 5

<210> SEQ ID NO 1
<211> LENGTH: 15
<212> TYPE: PRT
<213> ORGANISM: Homo sapiens

<400> SEQUENCE: 1

Tyr Met Met Gly Asn Glu Leu Thr Phe Leu Asp Asp Ser Ile Cys
1               5                   10                  15

<210> SEQ ID NO 2
<211> LENGTH: 20
<212> TYPE: DNA
<213> ORGANISM: Artificial Sequence
<220> FEATURE:
<223> OTHER INFORMATION: Human
<220> FEATURE:
<221> NAME/KEY: primer_bind
<222> LOCATION: (1)..(20)

<400> SEQUENCE: 2
ccacatcgct cagacaccat                                          20

<210> SEQ ID NO 3
<211> LENGTH: 26
<212> TYPE: DNA
<213> ORGANISM: Artificial Sequence
<220> FEATURE:
<223> OTHER INFORMATION: Human
<220> FEATURE:
<221> NAME/KEY: primer_bind
<222> LOCATION: (1)..(26)

<400> SEQUENCE: 3
ggcaacaata tccactttac cagagt                                   26

<210> SEQ ID NO 4
```

-continued

```
<211> LENGTH: 23
<212> TYPE: DNA
<213> ORGANISM: Artificial Sequence
<220> FEATURE:
<223> OTHER INFORMATION: Human
<220> FEATURE:
<221> NAME/KEY: primer_bind
<222> LOCATION: (1)..(23)

<400> SEQUENCE: 4
gaaacagcac attcccagag ttc                                    23

<210> SEQ ID NO 5
<211> LENGTH: 17
<212> TYPE: DNA
<213> ORGANISM: Artificial Sequence
<220> FEATURE:
<223> OTHER INFORMATION: Human
<220> FEATURE:
<221> NAME/KEY: primer_bind
<222> LOCATION: (1)..(17)

<400> SEQUENCE: 5
atggcccagc ggatgag                                           17
```

METHOD OF ISOLATING REGULATORY T CELLS FROM HUMAN SAMPLES

FIELD OF THE INVENTION

This invention relates to the study of human CTLA-4 (cytotoxic T lymphocyte antigen-4, or CD152) that represents an essential receptor involved in negative regulation of T cell activation. More particularly, it relates to the identification of an antigen specific to human CTLA-4 molecule, a complete human monoclonal antibody which specifically binds to the antigen, and various uses for the monoclonal antibody, such as detection and isolation agents.

REFERENCES

U.S. Pat. No. 5,811,097.
U.S. Pat. No. 5,855,887.
U.S. Pat. No. 6,051,227.
U.S. Pat. No. 6,207,156.
U.S. Pat. No. 6,228,361
U.S. Pat. No. 7,229,628.
WO 2005/012495.
WO 2007/117602.
Birebent, B, et al, 2004, "Suppressive properties of human CD4+ CD25+ regulatory T cells are dependent on CTLA-4 expression," *Eur. J. Immunol.*, 34:3485-96.
Burstein, S and Knapp, R, 1977, "Chemotherapy of murine ovarian carcinoma by methotrexate-antibody conjugates," *J. Med. Chem.*, 20:950-2.
Chikuma, S and Bluestone, J A, 2002, "CTLA-4: acting at the synapse," *Mol. Interv.*, 2:205-8.
Chin, L T, et al, 2001, "Establishment and evaluation of mouse-human heteromyeloma cell lines obtained by electrofusion for immortalizing human immunoglobulins," *J. Biomed. Lab. Sci.*, 13:117-23.
Chin, L T, et al, 2007, "Site-directed in vitro immunization leads to a complete human monoclonal IgG4 lambda that binds specifically to the CDR2 region of CTLA-4 (CD152) without interfering the engagement of natural ligands," *BMC Biotechnol.*, 7:51.
Dannull, J, et al, 2005, "Enhancement of vaccine-mediated antitumor immunity in cancer patients after depletion of regulatory T cells," *J. Clin. Invest.*, 115:3623-33.
Davis, D M and Dustin, M L, 2004, "What is the importance of the immunological synapse?" *Trends Immunol.*, 25:323-7.
Duenas M, et al, 1996, "In vitro immunization of naive human B cells yields high affinity immunoglobulin G antibodies as illustrated by phage display," *Immunology*, 89:1-7.
Dustin, M L, 2002, "The immunological synapse," *Arthritis Res.*, 4 Suppl 3:S119-25.
Egen, J G and Allison, J P, 2002, "Cytotoxic T lymphocyte antigen-4 accumulation in the immunological synapse is regulated by TCR signal strength," *Immunity*, 16:23-35.
Egen, J G, et al, 2002, "CTLA-4: new insights into its biological function and use in tumor immunotherapy," *Nat. Immunol.*, 3:611-8.
Gough, S C, et al, 2005, "CTLA4 gene polymorphism and autoimmunity," *Immunol. Rev.*, 204:102-15.
Grakoui, A, et al, 1999, "The immunological synapse: a molecular machine controlling T cell activation," *Science*, 285:221-7.
Hori, S, et al, 2003, "Control of regulatory T cell development by the transcription factor Foxp3," *Science*, 299:1057-61.
Krummel, M F and Allison, J P, 1996, "CTLA-4 engagement inhibits IL-2 accumulation and cell cycle progression upon activation of resting T cells," *J. Exp. Med.*, 183:2533-40.
Linsley, P S, et al, 1991, "CTLA-4 is a second receptor for the B cell activation antigen B7," *J. Exp. Med.*, 174:561-9.
Linsley, P S, et al, 1992, "Coexpression and functional cooperation of CTLA-4 and CD28 on activated T lymphocytes," *J. Exp. Med.*, 176:1595-604.
Lopes, J E, et al, 2006, "Analysis of FOXP3 reveals multiple domains required for its function as a transcriptional repressor," *J. Immunol.*, 177, 3133-42.
Magistrelli, G, et al, 1999, "A soluble form of CTLA-4 generated by alternative splicing is expressed by nonstimulated human T cells," *Eur. J. Immunol.*, 29:3596-602.
Nistico, L, et al, 1996, "The CTLA-4 gene region of chromosome 2q33 is linked to, and associated with, type 1 diabetes. Belgian Diabetes Registry," *Hum. Mol. Genet.*, 5:1075-80.
Oaks, M K and Hallett, K M, 2000, "a soluble form of CTLA-4 in patients with autoimmune thyroid disease," *J. Immunol.*, 164:5015-8.
Oaks, M K, et al, 2000, "A native soluble form of CTLA-4," *Cell. Immunol.*, 201:144-53.
Peach, R J, et al, 1994, "Complementarity determining region 1 (CDR1)- and CDR3-analogous regions in CTLA-4 and CD28 determine the binding to B7-1," *J. Exp. Med.*, 180: 2049-58.
Pioli, C, et al, 2000, "Inhibition of IgG1 and IgE production by stimulation of the B cell CTLA-4 receptor" *J. Immunol.*, 165:5530-6.
Prud'homme, G J, 2004, "Altering immune tolerance therapeutically: the power of negative thinking," *J. Leukoc. Biol.*, 75:586-99.
Qi, S Y, et al, 2001, "Synaptic pattern formation during cellular recognition," *Proc. Natl. Acad. Sci. USA*, 98:6548-53.
Rao, A, et al, 2007, "Successful bone marrow transplantation for IPEX syndrome after reduced-intensity conditioning," *Blood*, 109:383-5.
Read, S, et al, 2006, "Blockade of CTLA-4 on CD4+ CD25+ regulatory T cells abrogates their function in vivo," *J. Immunol.*, 177:4376-83.
Sakaguchi, S, 2005, "Naturally arising Foxp3-expressing CD25+CD4+ regulatory T cells in immunological tolerance to self and non-self," *Nat. Immunol.*, 6:345-52.
Sato, S, et al, 2004, "Serum soluble CTLA-4 levels are increased in diffuse cutaneous systemic sclerosis," *Rheumatology*, 43:1261-6.
Schwartz, J C, et al, 2001, "Structural basis for co-stimulation by the human CTLA-4/B7-2 complex," *Nature*, 410:604-8.
Sharpe, A H and Freeman, G J, 2002, "The B7-CD28 superfamily" *Nat. Rev. Immunol.*, 2:116-26.
Stamper, C C, et al, 2001, "Crystal structure of the B7-1/CTLA-4 complex that inhibits human immune responses," *Nature*, 410:608-11.
Steiner, K, et al, 1999, "Enhanced expression of CTLA-4 (CD152) on CD4+ T cells in HIV infection," *Clin. Exp. Immunol.*, 115:451-7.
Takahashi, T, et al, 2000, "Immunologic self-tolerance maintained by CD25(+)CD4(+) regulatory T cells constitutively expressing cytotoxic T lymphocyte-associated antigen 4," *J. Exp. Med.*, 192:303-10.
Tivol, E A, et al, 1995, "Loss of CTLA-4 leads to massive lymphoproliferation and fatal multiorgan tissue destruction, revealing a critical negative regulatory role of CTLA-4," *Immunity*, 3:541-7.
von Boehmer, H, 2005, "Mechanisms of suppression by suppressor T cells," *Nat. Immunol.*, 6:338-44.

Wang, S and Chen, L, 2004, "T lymphocyte co-signaling pathways of the B7-CD28 family," *Cell. Mol. Immunol.*, 1:37-42.

Ward, F J and Barker, R N, 2007, "Soluble CTLA-4 responses—a novel mechanism for regulatory T cell suppression?" *Immunology*, 120, Suppl:9 (meeting abstract)

Wildin, R S and Freitas, A, 2005, "IPEX and FOXP3: clinical and research perspectives," *J. Autoimmun.*, 25 Suppl:56-62.

Wong, C K, et al, 2005, "Aberrant production of soluble costimulatory molecules CTLA-4, CD28, CD80 and CD86 in patients with systemic lupus erythematosus," *Rheumatology*, 44:989-94.

Wong, C K, et al, 2005, "Increased expression of plasma and cell surface co-stimulatory molecules CTLA-4, CD28 and CD86 in adult patients with allergic asthma," *Clin. Exp. Immunol.*, 141:122-9.

Wu, Y, et al, 2006, "FOXP3 controls regulatory T cell function through cooperation with NFAT," *Cell*, 126:375-87.

Xystrakis, E, et al, 2004, "Identification of a novel natural regulatory CD8 T-cell subset and analysis of its mechanism of regulation," *Blood*, 104:3294-301.

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

On-going studies of the collaboration scenarios between T cells and antigen-presenting cells (APCs) foresaw dramatic changes which have revealed some therapeutic targets and medicinal potentials in certain regards. For example, it has been shown that the specialized and dynamic molecular machinery, present in the tight junction between a T cell and an APC, regulates immunological responses (Dustin, 2002; Grakoui et al., 1999; Qi et al., 2001). It has also been inferred that the machinery, termed the immunological synapse, correlates with a high degree of intercellular communication controlling disparate biological process (Davis and Dustin, 2004). A number of molecules have been confined at the immunological synapse to ensure their interim expression and interaction at the right time and place thus the sum and integration of signals are relevant to evoke appropriate T cell responses. Within this limited and—μm-sized area is full of interacting molecules, of which CTLA-4 has been identified to be responsible for inhibiting T cell responses in a T cell receptor (TCR)-dependent manner (Chikuma and Bluestone, 2002; Egen and Allison, 2002).

Human CTLA-4 was mapped to band q33 of chromosome 2 and was classified into a group of immunomodulating receptors, collectively termed as CD28 superfamily (Sharpe and Freeman, 2002). As shown in FIG. 1, the complete cDNA sequence of human CTLA-4 (isoform A) has the Genbank accession number L15006 and the structure has the accession number 1AH1 in the Molecular Modeling DataBase (MMDB) of NCBI's structure database. The region of amino acids -35 to 0 is the singal peptide; 1-126 is the extracellular V-like domain; 123-151 is the transmembrane domain; and 152-188 is the cytoplasmic domain. It is well established that two members of this superfamily, CD28 and CTLA-4, have opposing functions and that CTLA-4 represents one of the major inhibitory receptors involved in co-stimulatory pathways regulating both humoral and cellular immune responses (Krummel and Allison, 1996; Linsley et al., 1991; Pioli et al., 2000). A majority of studies indicate that CD28 provides direct enhancement signals, including up-regulation/stabilization of cytokine gene transcription, improved cell survival, lowered threshold for activation, and cytoskeletal effects; however, information on the function of CTLA-4 is much less clear. Thus far, the most compelling evidence for an inhibitory role of CTLA-4 is derived from the deficient knockout mice (CTLA-4$^{-/-}$) (Tivol et al., 1995). These mice suffer from a fatal T-cell lymphoproliferative disorder with splenomegaly, lymphoadenopathy and hyper-responsive infiltration in several organs including heart that become apparent by four weeks after birth. This fetal disorder is presumably due to reactivities to multiple self-antigens, since the expression of a single transgenic TCR prevents this disease. The TCR-dependent activation in these knockout mice appears to require CD28 costimulation, because CTLA-4$^{-/-}$CD28$^{-/-}$ mice do not suffer the lymphoproliferative disease. Likewise, treatment of these mice perinatally with soluble CTLA-4-Ig, which competes ligands access of cell surface CTLA-4, prevents such a disease effectively. Nonetheless, the mechanism of CTLA-4 action is still unclear, with no obvious central theme.

Conceptually, the interaction of CD28 on the lymphocyte with B7 proteins on the APC provides a necessary costimulatory second signal for a T cell to be able to fully respond to an antigen. The original family members in the pathway consist of two B7 ligands—CD80 (B7-1) and CD86 (B7-2), which have specificities towards the two receptors—CD28 and CTLA-4. CD28 is constitutively expressed on the surface of T cells whereas CTLA-4 surface expression is rapidly up-regulated to a limited extent following T cell activation. The kinetics of expression of CD80 and CD86 also differ. CD86 is constitutively expressed on interdigitating dendritic cells, Langerhans cells, peripheral blood dendritic cells, memory B cells and germinal center B cells. Furthermore, CD86 is expressed at low levels on monocytes, but its rapid up-regulation through IFN-γ stimulation has led to the hypothesis that CD86 functions primarily in initiating an immune response. On the other hand, CD80, being expressed later in time, may serve to amplify or regulate the response. Newly identified family members of the related molecules include: the inducible costimulatory molecule (ICOS), program death 1 (PD-1) receptor, B and T lymphocyte attenuator (BTLA), B7-H1, B7-H2, B7-H3, B7-H4, PD-1 ligand 1 (PD-L1) and PD-L2 (Wang and Chen, 2004). The novel interactions among these new family members underscore additional complexity of this costimulatory pathway in mounting an appropriate immune response.

A shorter soluble form of CTLA-4 lacking the transmembrane region has been achieved from RT-PCR cloning of non-activated T cells in animals as well as humans (Magistrelli et al., 1999; Oaks et al., 2000). Soluble CTLA-4 (sCTLA-4, CTLA-4 isoform B; FIG. 1) seems to be a fully functional CD80 and CD86 receptor, thus likely to affect T-cell responses in a paracrine manner. Furthermore, immunoreactive sCTLA-4 can be detected in the serum of 14/64 healthy subjects. In addition, the presence of high concentration of sCTLA-4 was observed in sera of patients with autoimmune thyroid diseases such as Graves' disease (Oaks and Hallett, 2000). Finally, recent reports show that sCTLA-4 levels are augmented in patients with autoimmune diseases, such as type-1 diabetes (Nistico et al., 1996), diffuse cutaneous systemic sclerosis (Sato et al., 2004), systemic lupus erythematosus (Wong et al. (2005) *Rheumatology* 44:989), and allergic asthma (Wong et al. (2005) *Clin. Exp. Immunol.* 141:122). It has been shown that activated T cells suppress sCTLA-4 mRNA expression and express preferentially the membrane-bound, full-length CTLA-4 (flCTLA-4) mRNA (Gough et al., 2005). Thus the ratio of sCTLA-4 to flCTLA-4 may have an important role in the regulation of immune homeostasis. The alternate transcripts or spliced variants of sCTLA-4, which lack the transmembrane encoding regions, were first deposited in the GenBank Sequence Database in humans, mice, and rats (accession numbers U90273, U90270, and U90271) in 1997 followed by a description of the same transcript in humans, being expressed by non-stimulated human T cells. The endogenous 174-aa soluble form, designed as isoform B, can be retrieved under the accession number NP_001032720.

It is also known in the field that immune reactivity is further controlled by various types of regulatory T cells (Tregs) (Sakaguchi, 2005). Tregs can be broadly divided into two subsets, i.e., the natural Treg cells of $CD4^+CD25^+$ phenotype, which constitute 5-10% of peripheral T cells, and the stimulation-induced (or adaptive) Treg cells identified in various models of inflammation, alloreactivity, or autoimmunity (Prud'homme, 2004). Recent findings suggest that the suppressive potential of $CD4^+CD25^+$ natural Tregs to other activated effector T cells is mediated by restricting early proliferation and the anti-effector function in inflamed tissues (von Boehmer, 2005). The forkhead-family transcription factor gene FOXP3, encoding the scurfin transcriptional regulator (Genbank accession number EF534714, NCBI protein accession number ABQ15210), has been implicated in the development and function of natural Tregs (Hori et al., 2003). A FOXP3 mutation in scurfy mice results in the absence of Tregs and early death from a multi-organ inflammatory disorder similar to the CTLA-4 or TGF-β deficiency. FOXP3 was shown to function as a transcriptional repressor, targeting composite NF-AT/AP-1 sites in cytokine gene promoters and the region responsible for NF-AT inhibition was mapped to the amino terminus (Lopes et al., 2006; Wu et al., 2006).

In principle, conventional techniques to isolate this rare Treg population often involve a two-step, multiple antibody selection procedure (Miltenyi Biotec, Bergisch Gladbach, Germany; BD Biosciences Pharmingen, San Jose, Calif.). Briefly, $CD4^+$ T lymphocytes are first preserved from not binding to a cocktail of mAbs that recognize other CD antigens expressed on erythrocytes, platelets, monocytes and peripheral leukocytes, etc. Subsequently, anti-human CD25 mAb positively selects the $CD25^+$ cells from the enriched $CD4^+$ cells, yielding $CD4^+CD25^+$ Treg cells. However, inevitably intermittent exposure to environmental pathogens results in traditional effector T cell activation and consequently expression of CD25 on human $CD4^+$ T cells, making identification of the Treg population a very difficult task. Additionally, even $CD4^-CD8^+$ natural Treg cells have been reported by Xystrakis et al. (2004) *Blood* 104: 3294-3301, indicating that Treg is a heterogeneous population. Furthermore, although FOXP3 expression is found predominantly within the Tregs, its intracellular nuclear localization causes direct detection impossible to live cells. Therefore, the characterization and application of Treg cells have been hampered by a lack of specific molecular markers on the surface of Tregs. A more complex approach was engineered to circumvent this particular problem, in which purified $CD4^+CD25^+$ peripheral blood mononuclear cells are further activated with agents such as ionomycin, and the Tregs are isolated based on binding to CTLA-4 blocking mAb (Birebent et al., 2004). Yet an even more complicated process has evolved by using additional surface markers like CD45RA and CD127 (WO 2007/117602).

Of interest is the association and potential synergism between the suppressive function of Tregs and the CTLA-4 expression. Unusually for non-activated T cells, Tregs constitutively express CTLA-4 (Takahashi et al., 2000), and CTLA-4 blockade on the Treg by specific blocking mAb can attenuate their suppressive activity, leading to the development of autoimmune disease in vivo (Read et al., 2006). In addition, it has been observed not only that the reported $CD4^-CD8^+$ natural Tregs express CTLA-4 (Xystrakis et al. 2004) but also that $CD4^+CD25^+$ cells further purified on the basis of recycling CTLA-4 are much more potent as regarding suppression (Birebent, et al., 2004). More importantly, the fact that inducible Tregs were the dominant source of sCTLA-4 was revealed in the 2007 British Society for Immunology Congress (Ward and Barker, 2007). Together, they indicate a strong correlation between CTLA-4 expression and suppressive regulatory function, supportive of the concept that CTLA-4 is functionally relevant to Tregs.

Because Tregs, in accompany with sCTLA-4, are involved in preventing allograft rejection and graft versus host disease and exert a dominant effect in controlling autoimmunity and maintaining peripheral tolerance, specific immune therapies designed to isolate and then expand them may improve the clinical course of various T-cell mediated pathology. As CTLA-4 provides the most important attenuating costimulatory signals, it will be expected by one of skill in the art that these molecules offer new targets for immunotherapy and diagnostics.

Studies of the physiological function and practical uses of CTLA-4 became possible with the isolation of monoclonal antibodies (mAbs). The first reported mouse anti-human CTLA-4 mAb (clone 11D4) suggested that blocking CTLA-4 signaling might deliver a positive signal synergizes with that delivered by CD28 (Linsley et al., 1992). The immune-enhancing nature of CTLA-4 antagonism has thus opened the possibility for a readily applicable tumor immunotherapy by temporary removal of CTLA-4-mediated inhibition using antagonistic Abs (Egen et al., 2002). Although the mechanisms by which CTLA-4 regulates T cell responses are not completely understood, blocking its activity with an antagonistic or blocking mAb offers a novel approach that holds a promise for immunotherapy. A set of corresponding U.S. patents such as U.S. Pat. No. 5,811,097, U.S. Pat. No. 5,855,887, U.S. Pat. No. 6,051,227, U.S. Pat. No. 6,207,156 and U.S. Pat. No. 7,229,628, illustrates approach of CTLA-4 blockade to strongly enhance antitumor responses has been highly regarded for the treatment potentials.

The anti-CTLA4 blocking mAbs, e.g., clone BNI3 (Steiner et al., 1999) (commercially available from BD Pharmingen) and clone AS33 (Antibody Solutions, Mountain View, Calif.), are often in use to detect sCTLA-4 in biological fluid (Oaks and Hallett, 2000) and to purify Tregs from activated peripheral blood (Birebent, et al., 2004). However, these may not be the best available strategy. Structural analyses have shown that the human CTLA-4 protein is composed of disulfide-linked homodimers of extracellular immunoglobulin variable (IgV) domains, each domain consisting of two layered β-sheets with ten strands (A, A', B, C, C', C", D, E, F and G) that form three complementarity determining region (CDR)-like regions (Schwartz et al., 2001; Stamper et al., 2001). Together with one mutational study (Peach et al., 1994), these two structural studies have independently pointed out that CDR1-like (the B-C loop) and CDR3-like (the F-G loop) regions in CTLA-4 directly bind endogenous B7 ligands (CD80 and CD86), whereas CDR2's responsibility is very trivial if there is any. Therefore, although in the initial publications there is no definite information to describe the CTLA-4 epitope on which the blocking mAbs bind, antagonistic effects and the subsequent enhancement on T-cell activation may be mediated by mAb competition that results from specific binding with amino acid residues on or close to a room encompassing CDR1 and CDR3. Thus uses of blocking mAbs in pair or in combination with endogenous B7 ligands provide a possible limitation caused by steric hindrances.

SUMMARY OF THE INVENTION

In one aspect, the present invention pertains to the discovery herein that potions other than CDR1 and CDR3 of human CTLA-4, such as the Met 55-cored CDR2-like sequence, do not play a role in binding of B7 ligands. Accordingly, mAbs that recognize a pre-determined Met 55-cored region can be used and are particularly useful to detect sCTLA-4 and/or to purify Tregs. To explore the effect of this Met 55-cored CDR2-like sequence, the inventors have recently developed and had possession of a complete human monoclonal IgG4λ targeting this particular stretch (Chin et al., 2007). As the mAb is capable, under the condition that the binding of a natural agonist was not interrupted, to mediate high (nanomolar) affinity binding to an extracellular constituency encompassing the CDR2-like region of CTLA-4, whereby it can react to activated human CD3+ cells, thus the invention can further provide a method for detecting sCTLA-4 and/or isolation Tregs.

The method contemplated herein may lead to an increase in sensitivity for sCTLA-4 detection and thus may be used to diagnose those conditions in which disease activity is tightly associated with sCTLA-4 production. Assays of interest include ELISA, RIA, FIA and flow cytometry, etc. In one embodiment, the agent is selected from the group consisting of: an antibody to CDR2 region of CTLA-4, a blocking antibody to CTLA-4, or a preferred combination of an antibody to CDR2 region of CTLA-4 and labeled human CD80. Binding may be quantified by a variety of methods known in the art. After an incubation period sufficient to allow the binding to reach equilibrium, the insoluble support is washed, and the remaining label quantified. The preferred agents in combination will enhance the detected label in the presence of sCTLA-4 and thus increase the detection limit.

On the other hand, the present invention may lead to an increase in efficiency for Treg isolation and encompasses both in vitro and in vivo methods. For in vitro uses, the cell intrinsically possessing the CTLA-4 receptor without prior activation, i.e., Tregs, may be purified from peripheral blood mononuclear cells. Efficient purification strategies are known in the art, including depletion and enrichment. Strategies of interest include magnetic cell separation, panning, bead-based chromatography and cytometry sorting, etc. As an example, purified mAb can be bound to an insoluble support, e.g. microtiter plate, magnetic beads, etc. The candidate cells are added to the support, and the unbound components are then washed off. The target cells are finally purified or isolated by elution. As to in vivo methods, the Treg may be present in a mammal, especially a human subject such as one who is suffering from declined or excessive Treg levels and who could benefit from a respective increase or decrease in Treg cells. Potential patients include those who have low or no level of Treg and develop autoimmune diseases that require Treg transfusion (Rao et al., 2007; Wildin and Freitas, 2005), or those who undergone adoptive immunotherapy that demand Treg reduction (Dannull et al., 2005). Thus, the invention provides a method for repopulating Treg cells in a human comprising administering to the human a therapeutically effective amount of a mAb.

In an embodiment, the invention provides antibodies that specifically bind to the Met 55-cored CDR2-like region of human CTLA-4. Preferred antibodies are monoclonal antibodies (mAbs) which are non-immunogenic in a human and bind to an epitope in the extracellular domain of CTLA-4. A preferred form of mAbs is human monoclonal IgG4λ, or a fragment thereof. More preferably, suitable mAbs will have an equilibrium dissociation constant (Kd) at least about $10^{-6}$ M toward human CTLA-4, more preferably at least about $10^{-8}$ M. The antibody is preferably an IgG antibody, particularly IgG4.

According to a further aspect, the invention is concerned with the CTLA-4 and a soluble form of this particular receptor which is the CTLA-4 extracellular domain. The mAbs against the Met 55-cored CDR2-like region are optionally conjugated with, or fused to, molecules which increase the serum half-lives thereof and can be formulated as pharmaceutical compositions comprising the mAbs and a physiologically acceptable carrier. Antibodies which bind to the Met 55-cored CDR2-like region may optionally be fused to a heterologous polypeptide or magnetic particles and the antibody or fusion thereof may be used to isolate and purify CTLA-4.

In further embodiments, antibodies which bind to CTLA-4 may optionally be fused or linked to a toxin and the antibody or fusion thereof may be used to separate or kill Treg cells from a source of human lymphocytes. Methods to fuse or link are known in the art, including genetic and chemical techniques. Genetic manipulations may include constructing an artificial nucleic acid segment consists of amino acid residues of a toxin molecule and antigen-binding domains derived from a mAb and producing said construct in a proper host, as described in WO 2005/012495. The immunotoxin may also be obtained from chemical conjugations such as using a heterobifunctional reagent (e.g., N-succinimidyl 3-(2-pyridyldithio)propionate), carbodiimide linkage or mixed anhydride procedure (Burstein and Knapp, 1977). The toxin moiety can be, e.g., any of the following toxic polypeptides: ricin, pseudomonas exotoxin, bryodin, diphtheria toxin, gelonin, α-sarcin, aspergillin, restrictocin, angiogenin, saporin, abrin, pokeweed antiviral protein, or a functional fragment of any of these toxic polypeptides.

BRIEF DESCRIPTION OF THE DRAWINGS

FIG. 1 shows the complete protein sequence of human CTLA-4 isoforms A and B with critical amino acids corresponding to CDR1, 2 and 3 are indicated. Asterisks indicate amino acid identity.

In FIG. 6A, detection of FOXP3 gene expression relative to GAPDH expression by real-time PCR analysis in purified $CD4^+CD25^-$ (■), $CD4^+CD25^+$ (▲) and $CTLA-4^+$ (▼) T cells from three normal donors is shown. Shown in FIG. 6B, pronounced enhancements, as compared with the control group (■), in the kinetics of thymidine incorporation were observed when Tregs were removed by the uses of $CTLA-4^+$ (▼) or anti-CTLA-4-diphtheria toxin conjugate (▲). It was difficult to consistently recover $CD4^-CD25^-$ population and thus omitted from the analysis. The proliferation response of $CD4^+CD25^+$ (○) and $CTLA-4^+$ cells (▽) is indicated. The data represent the mean of triplicate samples.

DETAILED DESCRIPTION OF THE INVENTION

Figure 2:
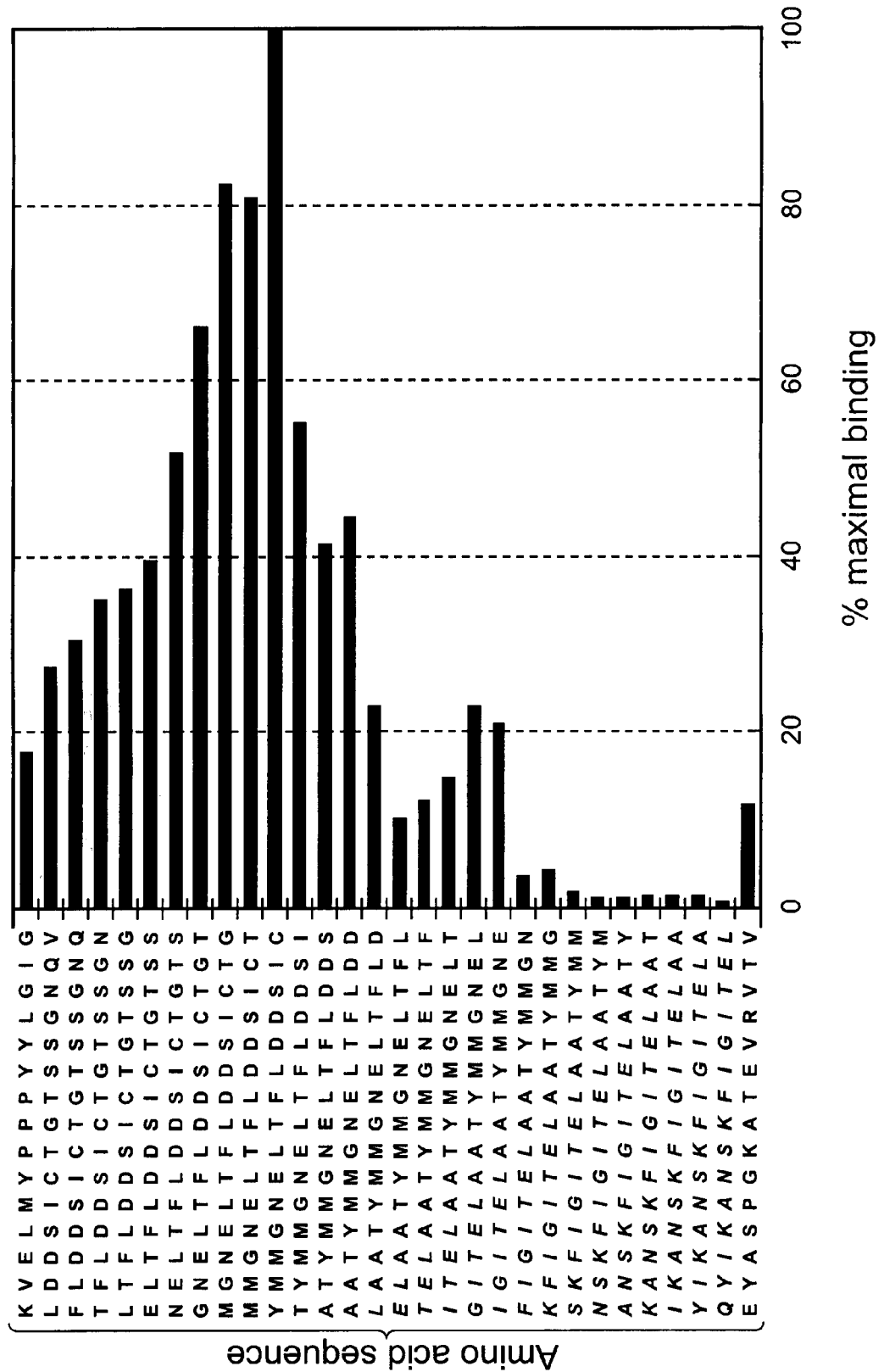
FIG. 2 illustrates the immunoblot screening of peptide arrays denotes the mAb specificity against the Met 55-cored CDR2-like region of human CTLA-4. 1 μg/ml of purified mAb was used to determine the binding epitope. Sequences of EYASPGKATEVRVTV, KVELMYPPPYYLGIG and QYIKANSKFIGITEL indicate CDR1-encompassing region, CDR3-encompassing region and T cell epitope (italic) used for site-directed immunization, respectively.

In describing the present invention, the following terms will be employed, and are intended to be defined as indicated below.

DEFINITIONS

A "complete human antibody" is an antibody containing exclusively human sequences. The antibody is preferably a monoclonal antibody. The terms "CTLA-4" when used herein encompass the native human sequence of CTLA-4 isoform A (FIG. 1). Optionally, the CTLA-4 is not associated with native glycosylation. "Native glycosylation" refers to the carbohydrate moieties which are covalently attached to CTLA-4 when it is produced in the mammalian cell from which it is derived in nature. Accordingly, human CTLA-4 produced in a non-human cell is an example of a CTLA-4 which is "not associated with native glycosylation". Sometimes, CTLA-4 is unglycosylated as a result of being produced recombinantly in a prokaryote or being synthesized chemically.

"Soluble CTLA-4" or "sCTLA-4" is a CTLA-4 molecule which contains neither a transmembrane domain nor a cytoplasmic tail and represents the native human sequence of CTLA-4 isoform B (FIG. 1). The "CTLA-4 extracellular domain" is a form of CTLA-4 which is essentially free of the transmembrane and cytoplasmic domains of CTLA-4. Ordinarily, the "CTLA-4 extracellular domain" will have an amino acid sequence of least about 95% amino acid sequence identity with the amino acid sequence of CTLA-4 isoform B indicated in FIG. 1, preferably includes CDR1-, CDR2- and CDR3-like regions.

An "antigenic function" means possession of an epitope or antigenic site that is capable of cross-reacting with antibodies raised against a native sequence of CTLA-4 defined by the CDR-like regions. The principal antigenic function of a CDR2-like region is that it does not involve in binding of CTLA-4, sCTLA-4 or CTLA-4 extracellular domain to B7 molecules.

"Immunize" a cell or an animal with an antigen refers to the action of exposing the cell or the animal to the antigen. The cell or animal can be immunized in any manner that leads to contact between the cell or the animal with the antigen.

A "heteromyeloma cell line" is a cell line derived from fusion of two different myeloma cells. The two different myeloma cells are preferably a human myeloma cell and a murine myeloma cell. Heteromyeloma cell lines are known in the art. For example, U.S. Pat. No. 6,228,361 and Chin et al., 2001 describe the preparation, characterization and use of various heteromyeloma cell lines.

A "fusion partner" is a cell that can be used to fuse with an antibody-producing cell for a beneficial purpose. Typically, the fusion leads to prolonged antibody production. Thus, without fusion to the fusion partner, the antibody-producing cell ceases to produce antibodies in culture. Upon fusion to the fusion partner, however, fused cells can be selected that produce antibodies in culture for at least about 3 months, preferably at least about 6, 9, 12, 18, 24 months or more. Fusion partners include, but are not limited to, myeloma cells and heteromyeloma cells.

An "agonist" is a molecule that can bind to cellular receptors, e.g., CTLA-4, and thus can produce various biological effects and initiate changes in cell function. Endogenous agonists are generally nature-occurring ligands such as neurotransmitters and, in the case of CTLA-4, CD80 and CD86. Exogenous agonists are commonly found as drugs.

An "antagonist" is a molecule that can bind to receptors, e.g., CTLA-4, but do not activate signal transduction mechanisms. The biological effects of a given antagonist are derived from preventing agonist binding and receptor activation, e.g., blocking mAbs.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period e.g., 8 to 14 days. It will be understood by one of skill in the art that a polypeptide of complete human origin typically represents "non-immunogenic in a human".

"Treating or ameliorating" a disease or medical condition means reducing or eliminating the symptoms of the disease or medical condition, or slowing down the progress of the disease/medical condition. The reduction is preferably at least about 10%, more preferably at least about 20%, 30%, 40%, 50%, 60%, 70%, 80% or 90%.

An "effective amount" is an amount of an agent that is sufficient to result in the intended effect. For example, for an antibody used to treat or ameliorate a disease, an effective amount is an amount of the antibody sufficient to reduce or eliminate the symptoms of the disease, or to slow down the progress of the disease.

A "sample" is an aliquot or a representative portion of a substance, material, or population. For example, a sample may be a sample of water, sewage, oil, sand, blood, biological tissue, urine or feces. A "biological sample" is a sample collected from or present within a biological subject, preferably a human subject.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

As used herein, the term "antibody" is used in the broadest sense and specifically covers monoclonal antibodies, antibody compositions with polyepitopic specificity, bispecific antibodies, diabodies, and single-chain molecules, as well as antibody fragments (e.g., Fab, $F(ab')_2$, and Fv), so long as they exhibit the desired biological activity.

The term "monoclonal antibody (mAb)" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site (epitope). The modifier "monoclonal" indicates the character of the antibody as being obtained from a substantially homogeneous population of antibodies, and is not to be construed as requiring production of the antibody by any particular method.

A "functional derivative" of a mAb is a compound having a qualitative biological property in common with a native mAb protein. "Functional derivatives" include, but are not limited to, fragments of native sequenced mAb, provided that they have a biological activity in common with a corresponding native sequenced mAb. The phrase "fragment" as used in connection with mAb fragmented derivatives, such as immunotoxins, provided that they have a biological activity in common with a corresponding native sequenced mAb.

A "magnetic cell separation" or "magnetic flow sorting" is a technique of cell selection based on achieving steady-state isolation between magnetic and non-magnetic cell streams in a flowing suspension. The selectivity depends upon cell tagging with cell surface marker antibodies labeled with a magnetic colloid. The characteristic feature of the method is its capability to fractionate cells based on the surface antigen expression. In order to perform this technique for the purpose of positive selection or depletion of cells labeled with human IgG4λ mAb (as described in Example 3), $1 \times 10^8$ single-cell suspension of PBMC can be first labeled with the mAb at 20 µg/ml reaction buffer for 15 min at 4° C. After unbound mAb is removed by washing, 0.2 ml of mouse anti-Human IgG MicroBeads (Miltenyi Biotec) is added and develops 15 min at 4° C. Following washing steps to remove unbound MicroBeads, the resuspended cells are magnetically separated in a magnetic field provided by the manufacturer (VarioMACS Separator). This isolated cell population represents cells intrinsically express CTLA-4 on their surface, and thus stands for Tregs.

A "thymidine incorporation assay", which evaluates the capability of cells to expand, can be used to measure the suppression of T cell proliferation in response to a recall antigen by isolated Tregs. In order to perform this assay, $5 \times 10^5$/well PMBC from vaccinated donors are activated with 5 µg/ml of tetanus toxoid (TT) as described in Example 3. During TT-driven proliferation, the cells are plated out in 96-well culture dishes containing a test sample with or without isolated Tregs (such test samples are optionally diluted) and cultured for three to seven days in a cell culture incubator at 37° C. in 5% $CO_2$ and air. Proliferation was measured by $^3$H-thymidine incorporation. During the final 16 hours of an assay, 1 µCi of $^3$H-thymidine is added to each well for the last 16 and proliferation is measured by scintillation counting using a Packard TopCount® Microplate Scintillation Counter (PerkinElmer, Shelton, Conn.). Tregs are expected to induce a statistically significant decrease (to a P value of 0.05) in $^3$H-thymidine uptake, relative to control. Preferred Treg cells lead to a decrease in $^3$H-thymidine uptake which is at least 30% of that of the control.

MODES AND METHODS FOR CARRYING OUT
THE INVENTION

The present invention is based on the discovery of the human monoclonal IgG4λ mAbs against the Met 55-cored CDR2-like region of CTLA-4. The epitope thus defined is shared by both CTLA-4 and sCTLA-4. The experiments described herein demonstrate that this mAb is a complete human mAb which appears not to play a role in the binding of CTLA-4 to its endogenous B7 ligands. In particular, this antibody has been found to enhance CTLA-4-CD80 interaction in certain conditions, thus indicating that it may be used to detect sCTLA-4 in combination with human CD80. As the presence of nature ligands of CTLA-4 is common in preparation of peripheral blood mononuclear cells (PBMC), other uses for this mAb, e.g. single-step enrichment of human Tregs, will be apparent and evident from the following discussion. A description follows as to how such a mAb may be prepared.

Culture materials and reagents are known in the art and may be obtained commercially. The culture medium used is RPMI-1640 (HyClone, Logan, Utah), supplemented with 1× non-essential amino acids (Life Technologies, Gaithersburg, Md.), 10% fetal bovine serum (FBS; Life Technologies) and 50 µg/ml of gentamycin and kanamycin (Sinton Chemical & Pharmaceutical, Hsinchu, Taiwan). Purified and biotinylated human CTLA-4-murine Ig fusion protein (rhCTLA-4-murine Ig or CD152-muIg), CD80-muIg and CD86-muIg (Ancell, Bayport, Minn.) are used in antigen-specific and competing enzyme-linked immunosorbent assay (ELISA), together with peroxidase-labeled goat antibodies against human IgG and IgM (Zymed Laboratories, South San Francisco, Calif.) or avidin horseradish peroxidase (eBioscience, San Diego, Calif.) as the reporting system. The fluorochrome-conjugated mouse mAb against human IgGs and human CD3 (UCHT1; mouse IgG1), together with rat mAb against mouse IgG2a are commercially available from Becton Dickinson Immunocytometry Systems (San Jose, Calif.) and Abcam (Cambridge, UK). The anti-CD3 (OKT3; mouse IgG2a) uses for T cell activation and the antagonistic anti-CD152 (BNI3; mouse IgG2a) can be purchased from eBioscience and Abcam, respectively.

Complete human mAbs are produced from in vitro stimulation and culture techniques. Generally, plasma and buffy coat samples from healthy routine blood donors, screened negative for HIV-1/2, HTLV-I/II, HCV, HBsAg and containing normal levels of alanine transferase (ALT), can be obtained from local Blood Centers. PBMC are isolated by density centrifugation on Ficoll-Paque (GE Healthcare Bio-Sciences, Uppsala, Sweden) as described elsewhere. The resulting PBMC are magnetically labeled with CD45RO MACS® microbeads (Miltenyi) then separated by a VarioMACS™ (Miltenyi) instrument according to the manufacturer's instructions. The purified CD45RO$^+$ T cells are cultured at a density of $2\times10^6$ cells/ml in the culture medium supplemented with 50 μM 2-mercaptoethanol and 10 μg/ml pokeweed mitogen (PWM; Sigma, St. Louis, Mo.). After 24 h, cells are removed by 400×g centrifugation to collect CD45RO$^+$ T cell replacing factor. Removal of cytotoxic cell populations is similarly performed by using colloidal superparamagnetic microbeads conjugated to monoclonal anti-human CD8 and anti-CD56 antibodies (Miltenyi). Removal of IL-10-producing cells may be achieved by using rat anti-human IL-10 (SouthernBiotech, Birmingham, Ala.) and goat anti-rat IgG microbeads (Miltenyi).

Site-directed in vitro immunization is preformed by using cytotoxic cell-depleted PBMC based on a two-step principle. Primary immunization is performed by incubating the cells for 6 days in a medium containing 10 nM of the heterotopic peptide antigen (QYIKANSKFIGITELAATYMMGNELTFLDDSICT; Fine Research Biochem, Taoyuan, Taiwan), 50 μM 2-mercaptoethanol, 10% heat-inactivated human serum, 0.05 ng/ml recombinant human (rh) IL-2 (eBioscience), and 25% (v/v) CD45RO$^+$ T cell replacing factor. For secondary immunization, $3\times10^7$ primary-immunized cells are mixed with the peptide in a flask that had been immobilized overnight with 5 mg/ml of CD40L (CD154; eBioscience) together with $1\times10^7$ QYIKANSKFIGITEL (Fine Research Biochem)-stimulated CD4$^+$ T cells and 5 ng/ml rh IL-15 (eBioscience). The cells are cultured for 3-5 days in a medium supplemented with 5% human serum, 50 mM 2-mercaptoethanol and 10 nM heterotopic peptide antigen. The significance of differences between treated and control cultures can be established by a variety of statistical methods known in the art such as Student's t test.

Subsequently, the in vitro immunized cells are infected with Epstein-Barr virus (EBV) by virus-containing supernatant derived from the EBV-producing marmoset cell line B95-8 (American Type Culture Collection, ATCC CRL 1612). The infected cells are seeded at $10^5$/well in 96-well plates together with mytomycin (Kyowa Hakko Kogyo, Tokyo, Japan)-treated PBMC as feeder cells ($10^4$/well) for the establishment of lymphoblastoid cells and screened for Ab production by ELISA. CTLA-4-specific ELISA can be performed by coating 0.25 μg/ml purified rhCD152-muIg, 0.5 μg/ml monoclonal mouse IgG2a (mIgG2a; Ancell), 1 μg/ml bovine serum albumin (BSA; Sigma) or 1 μg/ml tetanus toxoid (TT; ADImmune, Taichung, Taiwan) onto microtitre plates overnight at 4° C. Culture supernatants are diluted to the desired level in 10 mM sodium phosphate buffer (pH 8.0), containing 0 5 M sodium chloride and 0.1% Tween-20. Coated plates are incubated with diluted culture supernatants, washed, incubated with peroxidase-labeled goat antibodies against human IgG and IgM and developed (15 min) by addition of 100 μl of the chromogenic substrate o-phenylaenediamine (OPD) (Sigma). The reaction is stopped after 30 min by adding 1 M sulphuric acid, and the absorbances are read at 490 nm.

Somatic cell hybridization can be generated by electrofusion. Briefly, CTLA-4-specific EBV-infected lymphoblastoid cells were fused with heteromyeloma cells (Chin et al., 2001) in an isotonic medium (280 mM sorbitol, 0.5 mM magnesium acetate, 0.1 mM calcium acetate and 1 mg/ml BSA; pH6.9-7.1). Cell fusion can be induced by high-voltage pulses using a BTX Electro Cell Manipulator ECM 2001 (Harvard Apparatus, Holliston, Mass.). CTLA-4-specific hybrids were selected and cloned by limiting dilution.

Instead of fusion, the in vitro immunized cells can be used to construct an antibody library, and the antibodies of interest are then identified from this library. Thus, after in vitro immunization, antibody-producing cells can be identified with the antigen (the cells at this stage can be optionally infected with EBV). A phage-display library is then constructed using these antibody-producing cells, and the phages containing the antibody fragment of interest can be identified by screening this library with the antigen. The methods of constructing phage display libraries are known in the art (Duenas et al., 1996).

To define the specific epitope of human CTLA-4 recognized by the mAb, peptide arrays (Genesis Biotech, Taipei, Taiwan and Fine Research Biochem, Taoyuan, Taiwan) containing in-situ synthesized peptides immobilized on special membrane can be used. In brief, 1 μg/mL of protein A (Proteus MIDI kit, Pro-Chem, Littleton, Mass.)-purified mAb is incubated by shaking in room temperature for 2 h. After washing, the membrane-bound mAb can be then visualized by diluted anti-human IgG conjugated with peroxidase (Jackson ImmunoResearch Laboratories, West Grove, Pa.) and FAST-DAB™ (Sigma). The amount of bound mAb is calculated by Image-Pro Plus 4.5 software (Media Cybernetics, Silver Spring, Md.) on the scanned images.

Assays to determine affinity and specificity of binding are known in the art, including competitive and non-competitive assays. A non-competitive assay is preferred in this analysis. The affinity of the mAb can be determined against rhCTLA-4-murine Ig fusion protein with an IAsys® optical biosensor (Affinity Sensors, Cambridge, UK) according to the manufacturer's instructions. Briefly, 200 μg/ml dialyzed and diluted rhCTLA-4-murine Ig is immobilized on the activated surface of carboxymethyl dextran cuvettes in 10 mM of sodium acetate buffer at pH 3.8. After conditioning with 10 mM HCl, immobilization of 2 mg/mL CD152-muIg can result in a response of 1100 arc sec. This represents the highest immobilization response for CD152 and gives a ligate binding capacity ($R_{max}$) of 300 arc sec. Serial dilutions of the mAb in PBS, i.e. $1.34\times10^{-9}$ M, $6.70\times10^{-9}$ M, $1.34\times10^{-8}$ M, $2.68\times10^{-8}$ M and $5.36\times10^{-8}$ M, are added to the CD152-coated cuvettes (final volume, 50 μl). Affinity constants (Kd) are calculated from these measurements as $k_{diss}/k_{ass}$ by using the FASTFIT™ program provided by the manufacturer.

The present invention provides a novel method of measuring human sCTLA-4 in biological samples. To this end, we develop an immunoassay for quantification sCTLA-4, and show in Example 2 that a soluble form of CTLA-4 can be detected at least ten times of lower sensitivity as compared with a conventional method known in the art. For illustration, sandwich ELISAs are used for detection of sCTLA-4 in human serum. For this purpose, wells of a 96-well microtiter plate were coated with anti-CTLA4 blocking mAb (clone BNI3; BD Pharmingen) or non-blocking CTLA-4 mAb as the insoluble support. After saturation by bovine serum albumin, 1001 of a 1:3 dilution of the test samples are applied to the wells, and the plates are incubated for 60 min at room temperature and then wash to remove unbound material. Next, a reporting system containing either biotinylated anti-CTLA4 mAb (clone AS-33, Antibody Solutions) or biotinylated CD80-muIg (Ancell) is added, and the reactions are further incubated for 1 h. Reactions are developed using a streptavidinperoxidase complex (Zymed) and 3,39,5,59-tetramethyl-benzidine substrate. Optical density (OD) is read at 450 nm. A standard curve can be generated with the use of a dilution series of a commercially available CTLA4-Ig fusion protein (Ancell). Binding may be measured by a variety of methods known in the art. After an incubation period sufficient to allow the binding to reach equilibrium, the insoluble support is washed, and the remaining label quantified. Assays of interest include ELISA, RIA, FIA and flow cytometry, etc.

Also provided is a method of enriching Treg cells from a sample, comprising contacting a suitable sample with the antibody, or functional derivatives thereof, of the present invention so as to form an antibody-antigen complex between the antibody and any CTLA-4 present on the surface of cells in the sample, and detecting the presence of any complex so formed, thereby isolating in the sample the presence of extracellular CTLA-4. It is intended that the enriching of Tregs can be performed by using only one positive selection step, i.e., preserving cells specifically express extracellular CTLA-4. Therefore, both populations of Treg and non-Treg can be recovered with minimal in vitro manipulation and maximal viability. To this end, in Example 3, $1 \times 10^8$ single-cell suspension of PBMC can be first labeled with the mAb at 20 µg/ml reaction buffer for 15 min at 4° C. After unbound mAb is removed by washing, 0.2 ml of mouse anti-Human IgG MicroBeads (Miltenyi Biotec) is added and develops 15 min at 4° C. Following washing steps to remove unbound MicroBeads, the resuspended cells are magnetically separated in a magnetic field. This enriched cell population thus represents Treg cells intrinsically express CTLA-4 on their surface. Consequently, negatively selected non-Treg population can be subsequently stimulated, e.g., by a recall antigen, without prolonged selection steps and thus without compromise of their survival.

Also in Example 3, a functional derivative, i.e., immunotoxin, is prepared from conjugation of diphtheria toxin with purified IgG4λ. Purified IgG4λ mAb is mixed with six times excess of N-succinimidyl 3-(2-pyridyldithio)propionate (GE Healthcare Bio-Sciences) in PBS, and the mixture is allowed to react for 30 min at room temperature and then dialyzed against PBS. The modified IgG4λ is then mixed with three times excess of reduced diphtheria toxin (Merck Taiwan LTD., Taipei, Taiwan) and 10-fold concentrated PBS (10% of the total volume) and store for 36 h at 40° C. The product is dialyzed and concentrated with Macrosep® Centrifugal Devices (Pall Corporation, East Hills, N.Y.) equilibrated and washed with PBS.

Suitable samples which are useful in the methods of CTLA-4 detection and Treg isolation include, but are not limited to biological fluids from a human subject such as blood, nasal mucosal discharge, oral mucosal discharge, vaginal mucosal discharge, semen, purrulent exudates, anal mucosal discharge and synovial fluid. Samples may also include lymphoid tissues such as spleen, lymph nodes, thymus, bone marrow, tonsils and Peyer's patches. In one embodiment, the human antibody is labeled with an immunological retrievable marker, i.e., anti-human Ig antibody conjugated with magnetic beads. Such a specific binding may be retrieved by a variety of methods known in the art, including but not limited to direct labeling of the presented mAb, cell panning, and fluorescence-activated cell sorting.

It has been generally accepted that human $CD4^+CD25^+$ Treg cells express FOXP3, whereas $CD25^-$ T cells do not and the expression of FOXP3 in $CD4^+$ T cells correlates with their ability to function as Treg cells (Sakaguchi, 2005). In one embodiment, the expression of FOXP3 is quantified by quantitative real-time PCR (QPCR) analysis in which RNA is first extracted using an RNeasy Mini Kit (Qiagen, Valencia, Calif.) according to the manufacturer's instructions, and cDNA is then prepared with 2.5 µM random hexamers (Applied Biosystems Inc., Foster City, Calif.). Message levels can be quantified by real-time PCR System. Amplification is carried out in a total volume of 25 µl for 40 to 50 cycles of 15 seconds at 95° C., 1 minute at 60° C., and product may be detected using SYBR Green I dye (Molecular Probes Inc., Eugene, Oreg.). Samples are run in triplicate, and their relative expression was determined by normalizing expression of each target to GAPDH, and then comparing this normalized value to the normalized expression in a reference sample to calculate a fold-change value. Primers were designed so that amplicons spanned intron/exon boundaries to minimize amplification of genomic DNA. Primer sequences were as follows:

```
GAPDH:
5'-CCACATCGCTCAGACACCAT-3'          (SEQ ID NO: 2)
and

5'-GGCAACAATATCCACTTTACCAGAGT-3';   (SEQ ID NO: 3)

FOXP3:
5'-GAAACAGCACATTCCCAGAGTTC-3'       (SEQ ID NO: 4)
and

5'-ATGGCCCAGCGGATGAG-3'.            (SEQ ID NO: 5)
```

The antibody or its functional derivatives, e.g., immunotoxins, may be administered by any suitable method known in the art, such as via intravascular, intrathecal, intravenous, intramuscular, parenteral, subcutaneous, intramedullar, intraperitoneal, topical, oral, rectal, vaginal, nasal, pulmonary and intratumoral routes.

Compositions

Another aspect of the present invention provides a composition comprising a fully human antibody prepared according to the present invention. Preferably, the antibody binds to its antigen with a high affinity. The Kd is preferably about 100 nM or less, more preferably about 40 nM or less, yet more preferably about 10 nM or less, still more preferably about 4 nM or less, and most preferably about 1 nM or less. In particular, the antibody is capable of recognizing at least two related antigens, such as microbial antigens that are only different due to antigenic variation, or proteins encoded by alleles of the same gene.

This invention also includes pharmaceutical compositions that contain, as the active ingredient, one or more of the antibodies in combination with a pharmaceutically acceptable carrier or excipients. In preparing the compositions of this invention, the active ingredient/antibody is usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of solutions (particularly sterile injectable solutions), tablets, pills, powders, lozenges, sachets, cachets, elixirs, suspensions, emulsions, syrups, aerosols (as a solid or in a liquid medium), ointments containing, for example, up to 10% by weight of the antibody, soft and hard gelatin capsules, suppositories, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents;

emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The liquid forms in which the novel compositions of the present invention may be incorporated for administration by injection include aqueous solutions (such PBS), suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
h=hour
min=minute
µM=micromolar
mM=millimolar
M=molar
ml=milliliter
µl=microliter
mg=milligram
µg=microgram
ALT=alanine transferase
CDR=complementarity determining region
CTLA-4=cytotoxic T lymphocyte antigen-4
ELISA=enzyme-linked immunosorbent assay
FBS=fetal bovine serum
HBsAg=hepatitis B surface antigen
HCV=hepatitis C virus
HIV=human immunodeficiency virus
HTLV=human T-cell leukemia virus
IEF=isoelectric focusing
Ig=immunoglobulin
Kd=equilibrium dissociation (affinity) constant;
mAb=monoclonal antibody
PBMC=peripheral blood mononuclear cells
PBS=phosphate buffered saline (20 mM phosphate buffer, pH 7.2 containing 145 mM NaCl)
rh=recombinant human
Tregs=regulatory T cells
TT=tetanus toxoid Example 1

Characterization of Anti-Human CTLA-4 mAb a) Epitope Mapping

To characterize the nature of complete human mAb binding, epitope mapping was performed by the Western blotting method with arrays containing the overlapping pendecapeptides, encompassing CDR1-like (the B-C loop), CDR3-like (the F-G loop) and the Met 55-cored sequence localized between the C' and D strands of the CD152 extracellular portion. FIG. 2 depicts that only the peptide corresponding to the C-terminus of the Met 55-cored sequence ($^{54}$YMMGNELTFLDDSIC$^{68}$; SEQ ID NO:1) was best recognized by the mAb, and thus representing the epitope, while neither the promiscuous T-cell epitope used to boost in vitro stimulation, nor CDR1-like or CDR3-like region contributes to the binding. From this result, it can be concluded that the Ala 51, Ala 52, Thr 53 and Thr 69 are not essential for mAb recognition.

b) Immunological and Biochemical Natures of the mAb

Figure 3:
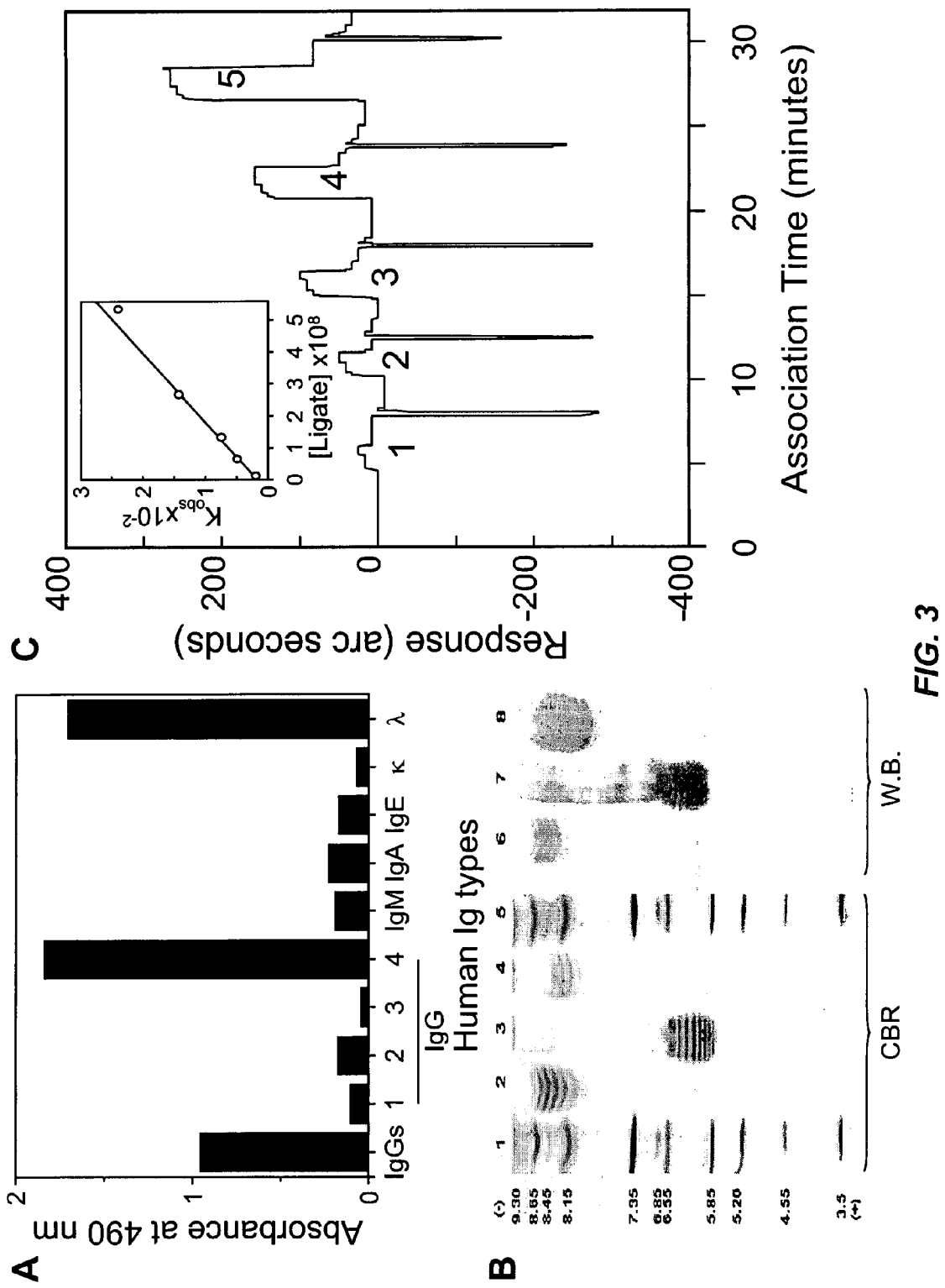
FIG. 3 demonstrates the immunological and biochemical natures of the anti-CTLA-4 mAb. Panel A shows isotyping and subtyping results by immobilizing anti-human Igs as indicated. The binding profile of the mAb was subsequently revealed by biotinylated CTLA-4-muIg and avidin-peroxidase conjugates. Results indicate that the present mAb belongs to a type of IgG4λ. Panel B indicates the isoelectric point of the monoclonal IgG4λ anti-CTLA-4 (lane 4 and 8), resolved by isoelectric focusing. Monoclonal human myeloma IgG1λ (lane 2 and 6) and IgG4λ (lane 3 and 7) were run in parallel for comparison. The electrophoretic patterns were visualized by either Coomassie brilliant blue staining (lane 1-5) or immunoblot (lane 6-8) with anti-human IgG conjugated with peroxidase and FAST™ DAB (Sigma). The calculated isoelectric points for human IgG1λ, IgG4λ and anti-CTLA-4 mAb to be approximately in the range of 7.92-8.79, 5.76-6.52 and 7.87-8.41, respectively, based on the calibration against the linear regression of standard protein markers. Panel C outlines the affinity determination by IAsys. Surface plasmon resonance obtained at 25° C. for increasing concentrations of anti-CTLA-4 mAb on purified, unlabeled CTLA-4-muIg. The straight line in the inset was obtained from the $k_{obs}$ plot versus ligated Ab concentration and yielded a $k_{diss}$ (the intercept) of 16.81 and a $k_{ass}$ value (the gradient) of $4.20 \times 10^9$. Therefore produced a Kd ($k_{diss}/k_{ass}$) of $4 \times 10^{-9}$ M.

The essentially pure mAb was isotyped and subtyped by solid phase ELISA, utilizing its reactivity with human CTLA-4 and appropriate immobilized typing Abs. The binding depicts the simultaneous presence of γ4 and λ chains in the mAb while other Ig chains are absent (FIG. 3A), thus the mAb has a γ4λ human Ig phenotype. Additionally, to compare the clonal nature with existing human monoclonal IgG1λ and IgG4λ derived from purified myeloma proteins, the isoelectric focusing (IEF) patterns were subsequently visualized. The resolvable bands, as shown in FIG. 3B, indicate that the presented mAb has a slightly lower yet basic pI similar to the IgG1λ, but in contrast to the acidic IgG4λ myeloma protein or to the anionic (pI 4.5-5.0) species of proteins commonly described for polyclonal IgG4. Western blot confirmed the purity of the Ab samples as illustrated by the anti-λ staining configurations. As shown in FIG. 3B, the corresponding pI of the myeloid IgG1λ, IgG4λ and the presented mAb obtained with linear regression of pH gradient were 7.92-8.79, 5.76-6.52 and 7.87-8.41, respectively. The equilibrium dissociation constant (Kd) for the purified intact mAb was determined by an IAsys analysis. The rate constant was evaluated directly from the sensogram using five cycles of soluble mAb binding to the immobilized rhCTLA-4-muIg. FIG. 3D reveals that, with the analysis of extent and association in single phase, the Kd was deduced to be $4 \times 10^{-9}$M.

c) Little or No Competition to B7-CD152 Binding of the mAb

Figure 4:
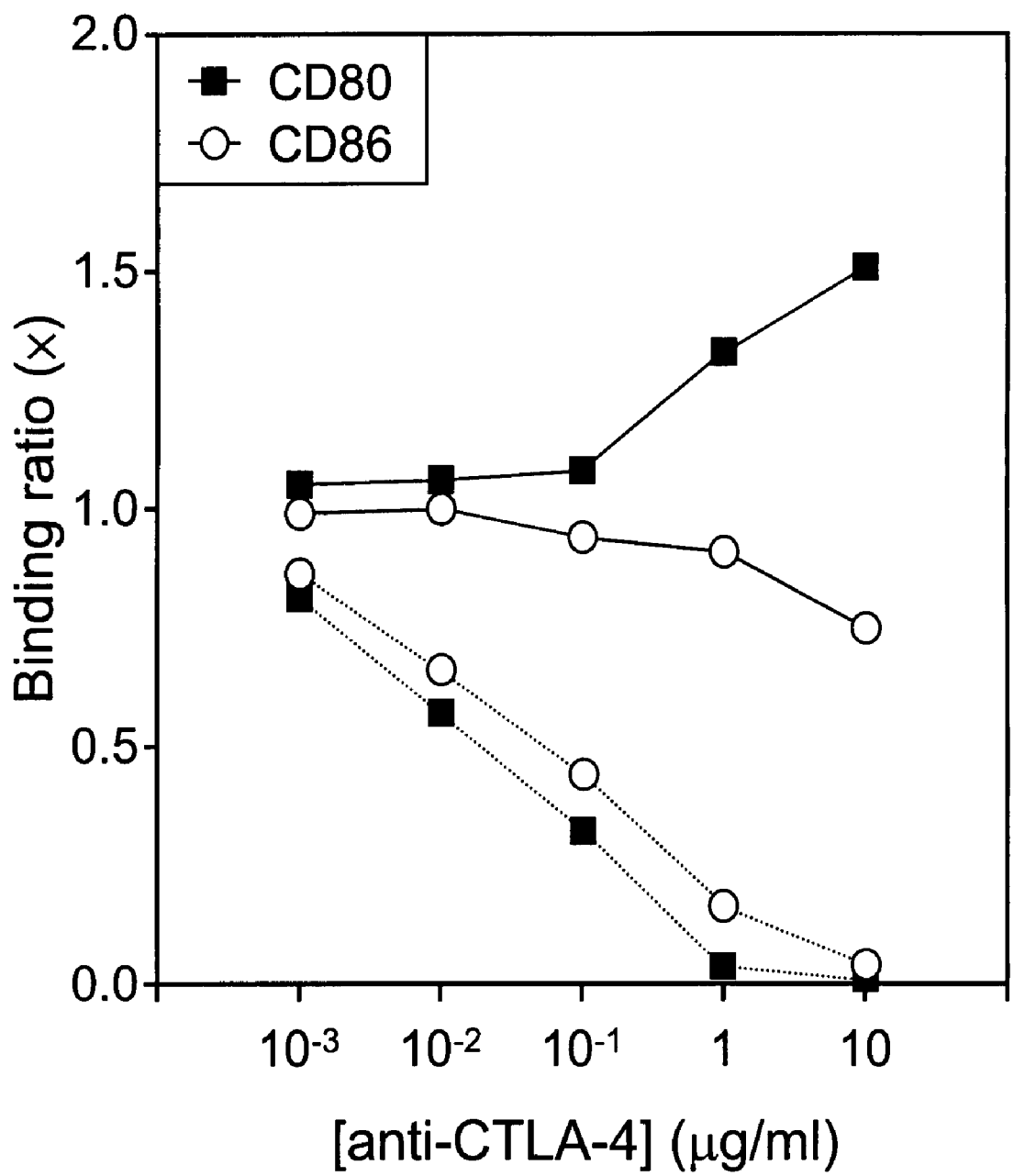
FIG. 4 indicates the binding of the present anti-CTLA-4 and CD80/CD86 agonists to human CTLA-4 are not mutually exclusive. Results obtained from ligand competition assays that test the ability of the complete human monoclonal anti-CTLA-4 (solid line) and BNI3 (dashed line) anti-CTLA-4 to compete for the CD80/CD86 and CTLA-4 interactions. Biotinylated CD80-muIg or CD86-muIg plus indicated increasing concentrations of the mAbs ($10^{-3}$-10 µg/mL) were incubated in microtiter wells coated with purified CTLA-4-muIg. Bound CD80/CD86 was detected with avidin-peroxidase conjugate and a peroxidase substrate. The data shown are representative of three experiments.

Although the CDR2-containing epitope does not seem to be involved in the binding of endogenous cognate ligands (CD80 and CD86), the epitope might present an allosteric site for non-competitive inhibition. To investigate this possibility, rhCTLA-4-muIg was immobilized onto wells and either biotinylated CD80-muIg or CD86-muIg was used as a binding ligand in the presence of the mAb or BNI3, i.e., a CTLA-4 blocking mouse IgG2a mAb (Steiner, et al., 1999). FIG. 4 shows, in contrast with the expected dose-dependent inhibition of specific receptor binding by the antagonistic BNI3, the mAb could not compete binding significantly with either CD80-muIg or CD86-muIg. Surprisingly, high doses of the mAb display synergism with the natural ligand CD80 but not CD86 with a consequence up to 50% enrichment of CD80 binding to rhCTLA-4-muIg.

Example 2

Using CDR2-Specific Agent Increase the Detection Limits of Human CTLA-4

Figure 5:
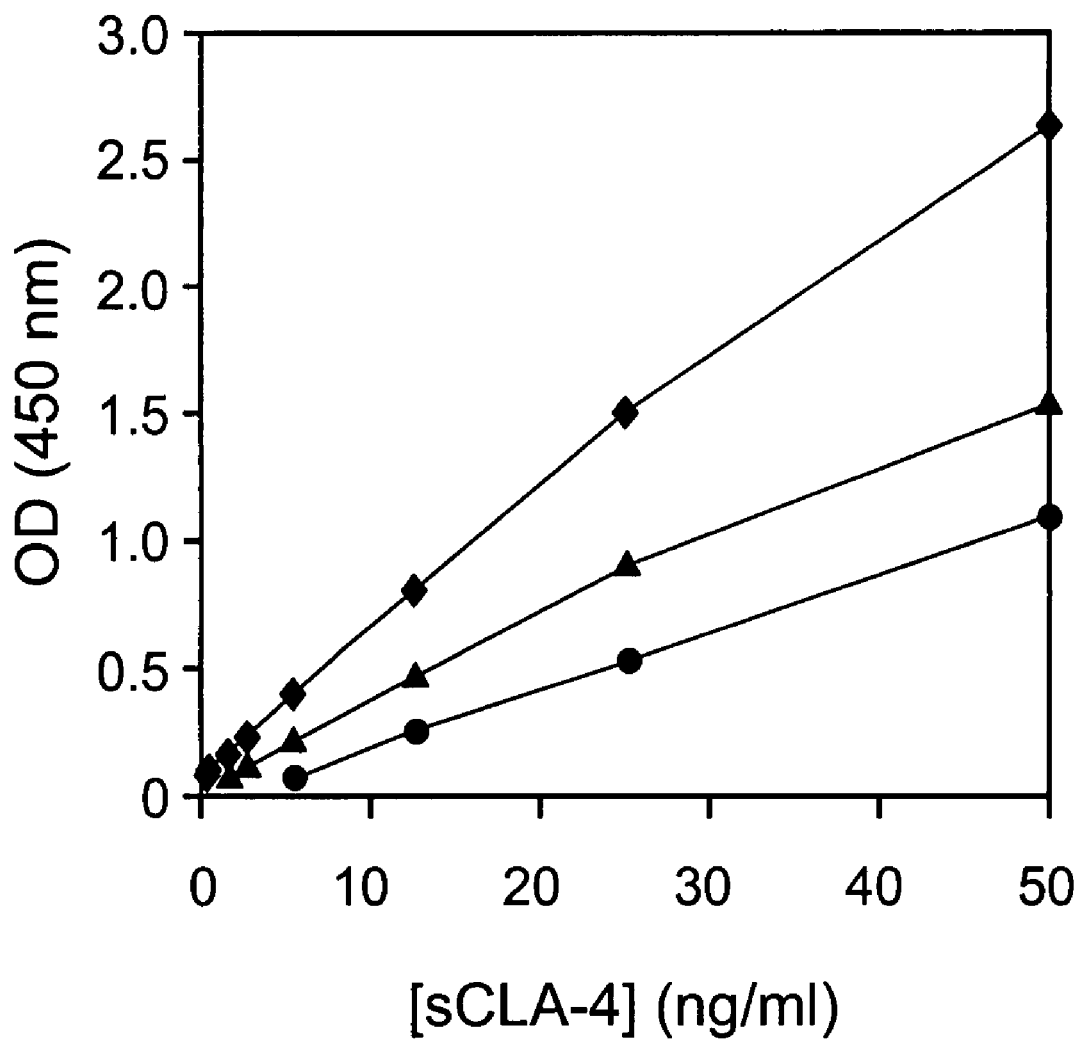
FIG. 5 is a representative combined data from the ELISA on human CTLA-4 detection, using available mAbs and recombinant human CD80 to CTLA-4. The assay was measured using commercially available CTLA4-muIg as a standard. ELISA analysis showing the limit of sensitivity of 0.39, 1.56 and 6.25 ng/ml for the assay using a pair of the human monoclonal IgG4λ and CD80 (♦), the human IgG4λ and BNI3 (▲) and blocking mAbs of BNI3 and AS-33 (●), respectively.

In practice, immunoassays based on the use of pairs of blocking Abs, which reactive with epitopes within the B7-binding region of the molecule; confront a primary limitation of steric hindrance. Blocking Abs may compete with each other and with endogenous CD80 and CD86 for the restricted CDR1- and CDR3-like regions, making them difficult to distinguish native sCTLA-4 in an assay system. To determine whether the above CTLA-4 binding synergism with the natural ligand CD80 displayed by the mAb may contribute a lower sensitivity; the mAb was coupled with CD80 in detecting sCTLA-4. In brief, the ELISA system utilizing the IgG4λ-coated plate for capture and biotinylated CD80-muIg recombinant protein (Ancell) for detection, followed by streptavidin-peroxidase for color reaction. FIG. 5 shows a representative experiment. This combination predominantly resolves a range of CTLA-4 from 0.39 to 50 ng/ml, while the blocking mAb pair identifies 6.25 to 50 ng/ml under similar experimental conditions. Likewise, a higher resolution of 1.56 to 50 ng/ml was also observed when the present mAb was in use together with a blocking mAb. This is not only consistent with the predicted respective three-dimensional binding sites based on the previous studies (Linsley, et al., 1992; Schwartz, et al., 2001; Stamper, et al., 2001) but also demonstrative that CTLA-4 mAb with CDR2-like region specificity, in combination with agents of CDR1- and CDR3-like specificities, increases the detection limits of CTLA-4.

Example 3

Isolation of the Intrinsic CTLA-4+ Populations Resulted in Increased Foxp3 Expression and Suppression One of the major unresolved problems in the field of using Tregs as a promising alternative to the standard immunosuppression regime is how to develop a reliable method for their isolation. Most prior arts reported to date exploit a negative selection non-CD4+ cells and a positive selection CD25+ cells, which is time-consuming and experience-dependent to manipulate human PBMC. However, having acknowledged the importance of CTLA-4 in Treg's function (Read, et al., 2006; Ward and Barker, 2007), the present invention turned the attention to utilize intrinsic CTLA-4 surface expression for Treg isolation. In particular, we asked if the non-blocking anti-CTLA-4 mAb provides a single positive selection for Teg cells. To address this question, we employed a thymidine incorporation assay to detect the suppression of built-in Tregs and the enhancement of Treg removal.

Figure 6A:
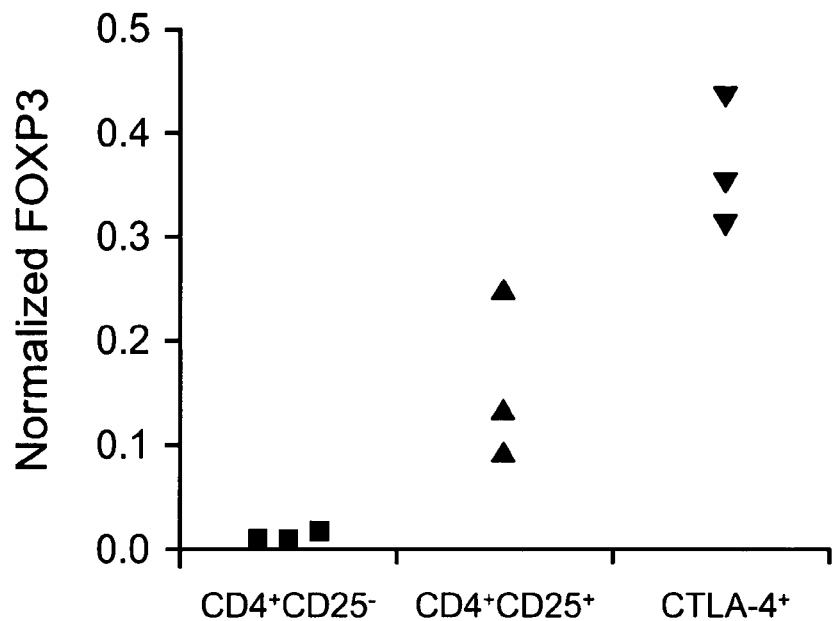
FIGS. 6A and 6B present the effect of isolating Tregs based on intrinsic CTLA-4 surface expression.
Figure 6B:
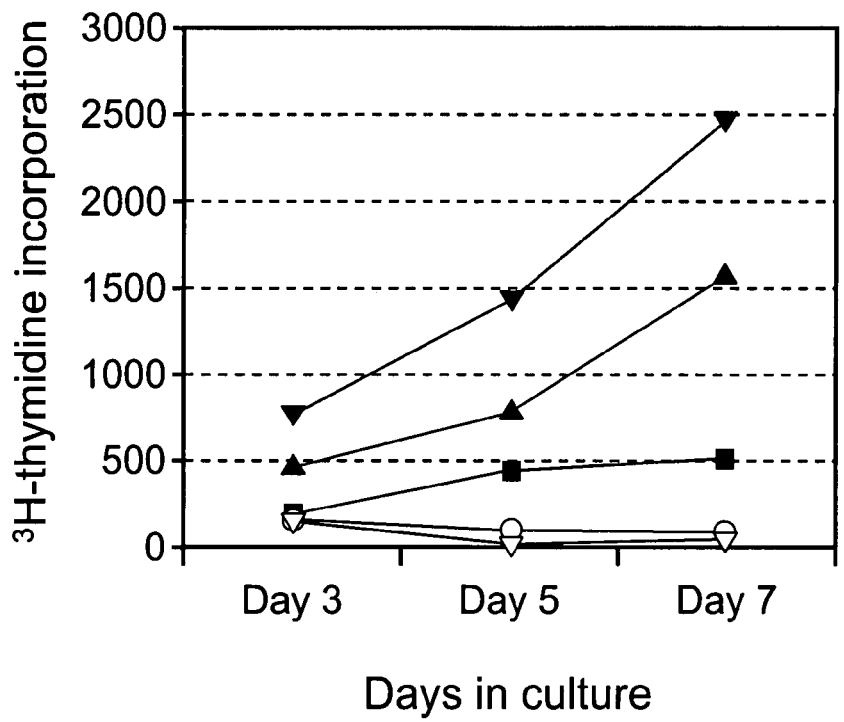

By analyzing the subsets from the in vitro tetanus toxoid stimulation for proliferation, removal of CTLA-4+ population is of great benefit to a recall response (FIG. 6B), further arguing that this is a Treg population. In some donors, the majority of CD4−CD25− cells could be recovered from the bound magnetic beads, but not from other donors. It is not known what causes the variability among donors. The identity of the population that upregulated CTLA-4 surface expression was also determined. The cells which upregulated CTLA-4 expression were enriched for Treg cells, and this supported by the fact that these cells retained antigen unresponsiveness similar to the purified CD4+CD25+ population. Because CD4+CD25+ cells predominantly represent Tregs and CTLA-4 surface expression is associated with an even higher FOXP3 expression, it was thus confirmed that CTLA-4+ cells symbolize regulatory T cells.

What is claimed is:

1. A method of enriching regulatory T cells from human samples, said method comprising:
   (a) contacting a population of suspended cells in a sample with a CTLA-4 non-blocking agent that recognizes the extracellular domain of CTLA-4, wherein said CTLA-4 non-blocking agent is non-immunogenic in a human and comprises an antibody or an antigen-binding fragment thereof; and
   (b) selecting cells that bind to the CTLA-4 non-blocking agent, wherein the selected cells are enriched for regulatory T cells.

2. The method of claim 1, wherein
   the non-blocking agent is a human monoclonal antibody which recognizes human CTLA-4 with a Kd of about 4 nM or less.

3. The method of claim 1, wherein
   the non-blocking agent is a human IgG4λ antibody.

* * * * *